United States Patent
Shimada et al.

(10) Patent No.: US 7,326,193 B2
(45) Date of Patent: Feb. 5, 2008

(54) DISPOSABLE PANTS-TYPE WEARING ARTICLE

(75) Inventors: Takaaki Shimada, Kagawa-ken (JP); Shunsuke Takino, Kagawa-ken (JP); Takashi Tsukayoshi, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 280 days.

(21) Appl. No.: 10/824,419

(22) Filed: Apr. 15, 2004

(65) Prior Publication Data

US 2004/0210204 A1 Oct. 21, 2004

(30) Foreign Application Priority Data

Apr. 18, 2003 (JP) .............................. 2003-114400

(51) Int. Cl.
*A61F 13/15* (2006.01)
(52) U.S. Cl. ........................... 604/385.201; 604/385.19
(58) Field of Classification Search ......... 604/385.201, 604/385.19
See application file for complete search history.

(56) References Cited

U.S. PATENT DOCUMENTS

| | | | |
|---|---|---|---|
| 3,196,874 A | 7/1965 | Hrubecky | |
| 3,710,797 A | 1/1973 | Marsan | |
| 3,724,464 A | 4/1973 | Enloe | |
| 3,744,494 A | 7/1973 | Marsan | |
| 3,774,610 A * | 11/1973 | Eckert et al. | ................ 604/365 |
| 3,848,595 A * | 11/1974 | Endres | ................ 604/385.201 |
| 3,860,004 A | 1/1975 | Nystrand | |
| 3,924,627 A * | 12/1975 | Nystrand | ................ 604/365 |
| 3,968,799 A * | 7/1976 | Schrading | ................ 604/365 |
| 4,067,336 A | 1/1978 | Johnson | |
| 4,182,334 A * | 1/1980 | Johnson | ............... 604/385.201 |
| 4,636,207 A | 1/1987 | Buell | |
| 4,675,012 A | 6/1987 | Rooyakkers | |
| 4,772,280 A | 9/1988 | Rooyakkers | |
| 4,946,454 A * | 8/1990 | Schmidt | ................ 604/385.19 |
| 5,021,051 A | 6/1991 | Hiuke | |
| 5,601,544 A | 2/1997 | Glaug et al. | |
| 5,746,730 A | 5/1998 | Suzuki et al. | |
| 6,102,892 A | 8/2000 | Putzer et al. | |
| 6,120,486 A | 9/2000 | Toyoda et al. | |
| 6,142,985 A | 11/2000 | Feist | |
| 6,152,908 A | 11/2000 | Widlund et al. | |
| 6,165,160 A | 12/2000 | Suzuki et al. | |
| 6,238,380 B1 | 5/2001 | Sasaki | |
| 6,440,117 B1 | 8/2002 | Itoh et al. | |

(Continued)

FOREIGN PATENT DOCUMENTS

EP 1177782 2/2002

(Continued)

*Primary Examiner*—Tatyana Zalukaeva
*Assistant Examiner*—C. Lynne Anderson
(74) *Attorney, Agent, or Firm*—Lowe, Hauptman, Ham & Berner LLP

(57) ABSTRACT

A disposable pants-type wearing article includes a body fluid absorbent assembly. In a crotch region of the wearing article, transversely opposite side edges of the body fluid absorbent assembly are respectively formed with folded portions so that a non-folded portion extending in from of the folded portions may have a relatively small extent and a non-folded portion extending behind the folded portions may have a relatively large extent.

16 Claims, 7 Drawing Sheets

U.S. PATENT DOCUMENTS

| | | |
|---|---|---|
| 6,613,955 B1 | 9/2003 | Lindsay et al. |
| 6,666,851 B2 | 12/2003 | Otsubo et al. |
| 2002/0068919 A1 | 6/2002 | Shinohara et al. |
| 2003/0163108 A1 | 8/2003 | Tears et al. |
| 2004/0133178 A1 | 7/2004 | Otsubo et al. |
| 2005/0004545 A1 | 1/2005 | Shimada et al. |
| 2005/0004548 A1 | 1/2005 | Otsubo et al. |
| 2005/0038404 A1 | 2/2005 | Takino et al. |
| 2005/0131375 A1 | 6/2005 | Sasaki et al. |
| 2005/0143711 A1 | 6/2005 | Otsubo et al. |
| 2005/0148989 A1 | 7/2005 | Otsubo et al. |
| 2005/0288648 A1 | 12/2005 | Otsubo et al. |

FOREIGN PATENT DOCUMENTS

| | | |
|---|---|---|
| EP | 1 219 273 A2 | 7/2002 |
| JP | 47-36734 | 12/1972 |
| JP | 48-20638 U | 3/1973 |
| JP | 50-33044 | 3/1975 |
| JP | 5021845 | 3/1975 |
| JP | 56-34345 | 4/1981 |
| JP | 60-163911 | 10/1985 |
| JP | 63-32516 U | 3/1988 |
| JP | 11188062 | 7/1999 |
| JP | 2002-035033 | 2/2002 |
| JP | 2003-10244 | 1/2003 |
| JP | 2003220091 | 8/2003 |
| JP | 2003230594 | 8/2003 |

\* cited by examiner

DISPOSABLE PANTS-TYPE WEARING ARTICLE

BACKGROUND OF THE INVENTION

The present invention relates to disposable pants-type wearing articles suitably used in the form of disposable diaper, training pants, adult pants for incontinence or the like. The present application is based on, and claims priority from, Japanese Application Serial Number 2003-114400, filed Apr. 18, 2003, the disclosure of which is hereby incorporated by reference herein in its entirety.

In disposable wearing articles such as disposable diapers including a rectangular body fluid absorbent panel, it is well known to fold transversely opposite sectors of the panel inwardly of the panel in a crotch region and thereby to form a pair of folded portions.

For example, in a diaper disclosed in Japanese Utility Model Application Publication No. 1972-36734A (Citation 1), the rectangular panel-like chassis has folded portions in a crotch region and each of these folded portions is symmetrically formed about a crossline bisecting a longitudinal dimension of the chassis. In other words, each of the folded portions is formed so as to be symmetric in a back-and-forth direction of the diaper.

A diaper disclosed in Japanese Patent Application Publication No. 1975-33044A (Citation 2) also is formed with the folded portions. These folded portions are formed by folding a rectangular body fluid absorbent panel-like material along a transverse center line and the lines radially extending from a midpoint of this transverse center line so that an inner surface of the diaper which are opposed to itself in these folded portions may be partially bonded together. The folded portions in this diaper also are symmetric about the transverse center line, in other words, as viewed in a back-and-forth direction of the diaper.

A pants-type wearing article disclosed in Japanese Patent Application Publication No. 2003-10244A (Citation 3) is adapted to be used in the form of disposable pants-type diaper or the like and includes a rectangular body fluid absorbent panel normally curved in U-shape and extending over a crotch region and further into front and rear waist regions. This panel also is provided in a crotch region with a pair of folded portions formed by folding the panel along a panel crossing line extending across a bottom of the pants-type wearing article and lines radially extending from a midpoint of a crossing line to transversely opposite side edges of the panel. In this wearing article also, each of these folded portions is symmetrically formed about the crossing line, in other words, symmetrically formed as viewed in a back-and-forth direction of the wearing article.

In every wearing article disclosed in Citations 1, 2 and 3, the folded portions of the panel in the crotch region function to locally reduce the width of the panel and, at the same time, function as the pockets adapted to contain bodily discharges.

It is common to the disclosures of Citations 1, 2 and 3 that the folded portions of the body fluid absorbent panel are symmetric as viewed in the back-and-forth direction of the diaper and the body fluid absorbent panel after the formation of these folded portions is also substantially symmetric as viewed in the back-and-forth direction of the diaper. The panels are destined to cover the wearer's back side with a rear zone of the panel extending behind the folded portions and to cover the wearer's belly side with the front zone of the panel extending in front of the folded portions. However, if the panel is dimensioned to be sufficiently wide to cover the wearer's hip with the rear zone of the panel in leakage-free fashion, the front zone of such wide panel will obstruct free movement of the wearer's legs. On the other hand, if the panel is dimensioned to be sufficiently narrow to avoid an anxiety that the front zone of the panel might obstruct free movement of the wearer's legs, the absorbing capacity of the panel in the vicinity of the wearer's hip will be insufficient to avoid leakage of body fluids.

SUMMARY OF THE INVENTION

In view of the problem as has been described above, it is an object of the present invention to provide a disposable pants-type wearing article wherein a body fluid absorbent assembly has a pair of folded portions in a crotch region improved to be free from an anxiety that the body fluid absorbent assembly might obstruct the movement of a diaper wearer's legs and might cause leakage of body fluids.

The object set forth above is achieved, according to the present invention, by a disposable pants-type wearing article comprising a front waist region, a rear waist region and a crotch region, the crotch region being provided with a body fluid absorbent assembly extending over the crotch region and further into the front and rear waist regions, the body fluid absorbent assembly having transversely opposite side edges extending generally parallel to each other into the front and rear waist regions and longitudinally curving in a generally U-shape with an inner surface thereof opposed to itself in the front and rear waist regions and, in the crotch region, the body fluid absorbent assembly having a pair of first folding guide lines extending from a midpoint of a crossline extending across the crotch region or from two points on the crossline which are equidistant in opposite directions from the midpoint to the transversely opposite side edges of the body fluid absorbent assembly placed aside toward the front waist region at a crossing angle $\alpha$ with respect to the crossline, a pair of second folding guide lines extending from the midpoint or the two points to the transversely opposite side edges of the body fluid absorbent assembly placed aside toward the rear waist region at a crossing angle $\beta$ with respect to the crossline, a pair of folded portions formed by folding inward respective sectors of the body fluid absorbent assembly defined between the first and second folding guide lines, a first non-folded portion extending aside from the pair of the first folding guide lines toward the front waist region and a second non-folded portion extending aside from the pair of the second folding guide lines toward the rear waist region.

The body fluid absorbent assembly is configured so that the first non-folded portion has a relatively small extent and the second non-folded portion has a relatively large extent.

The present invention includes the following embodiments.

The crossline extends across a bottom of the crotch region as viewed in a vertical direction of the wearing article and the crossing angle $\alpha$ is larger than the crossing angle $\beta$.

The crossline is placed aside from a bottom of the crotch region as viewed in the vertical direction of the wearing article toward the front waist region and the crossing angle $\alpha$ is equal to or larger than the crossing angle $\beta$.

The crossing angle $\alpha$ is in a range of 35 to 60° and the crossing angle $\beta$ is in a range of 10 to 30°.

The crossline is placed aside from the bottom of the crotch region toward the front waist region by 10 to 50 mm.

DETAILED DESCRIPTION OF THE PREFERRED EMBODIMENTS

Details of a disposable pants-type wearing article according to the present invention will be more fully understood from the description of a pants-type diaper as one embodiment of the invention given hereunder with reference to the accompanying drawings.

Figure 1:
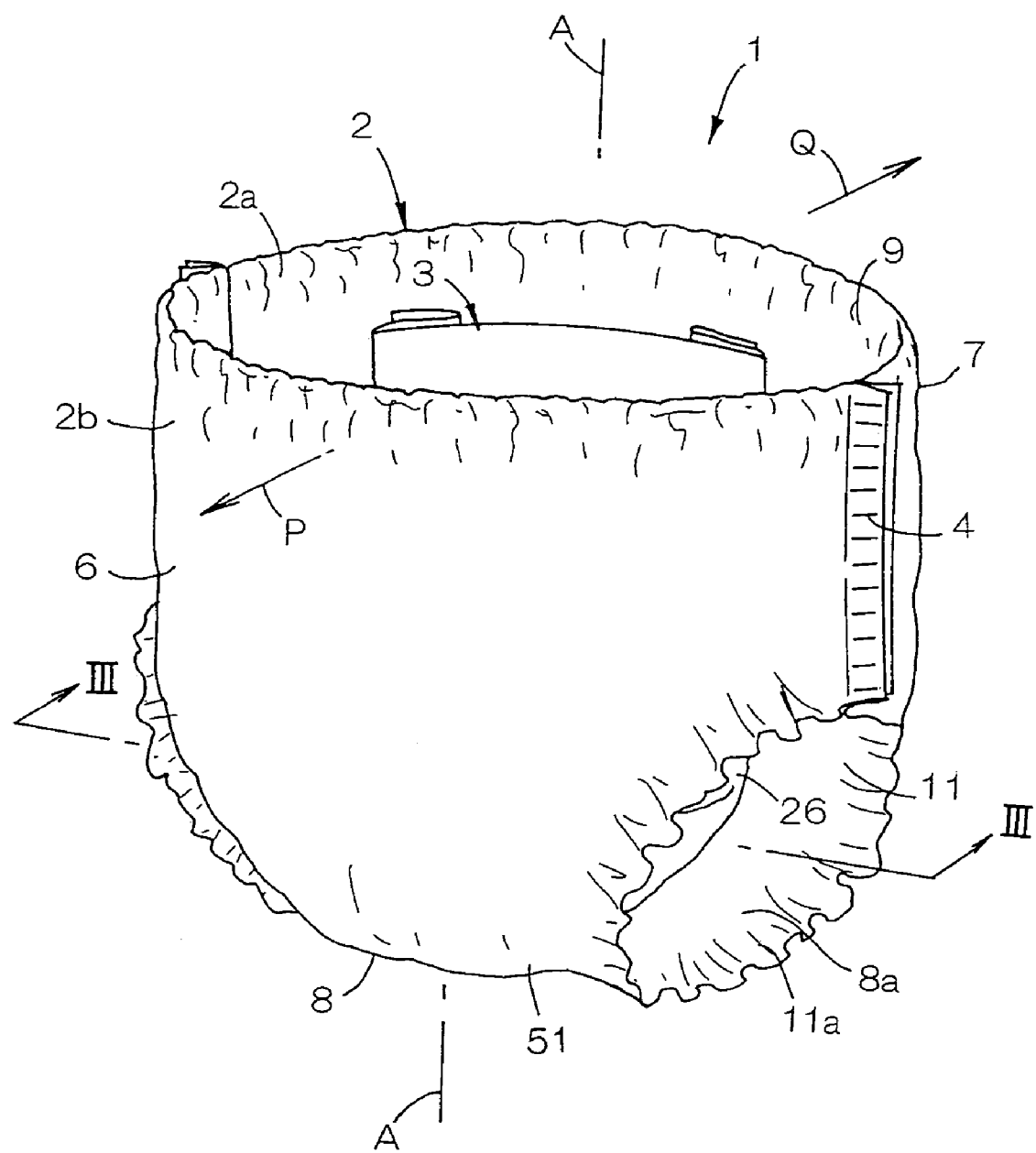
FIG. 1 is a perspective view of a pants-type disposable diaper.
Figure 2:
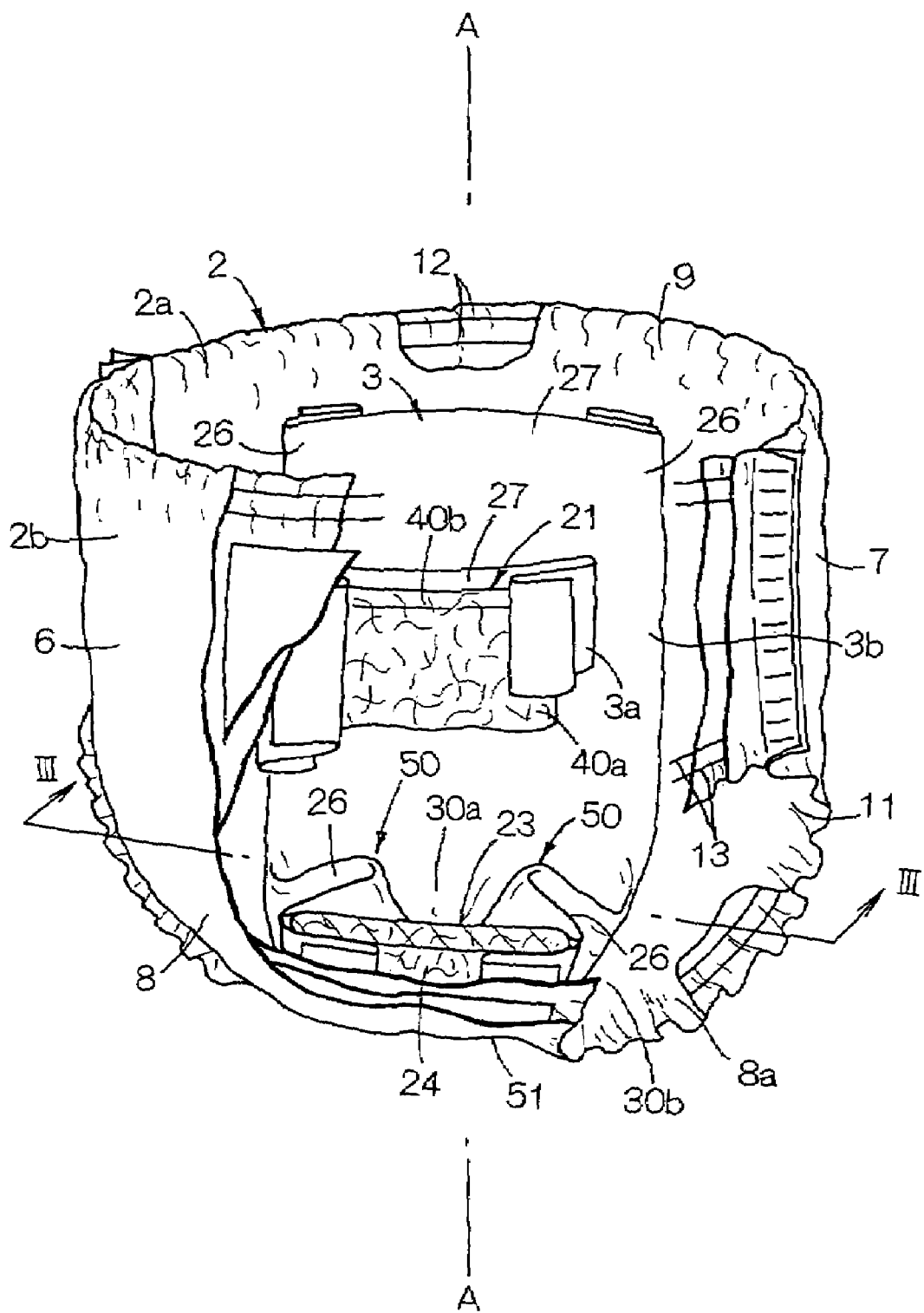
FIG. 2 is a partially cutaway perspective view of the diaper of FIG. 1.
Figure 3:
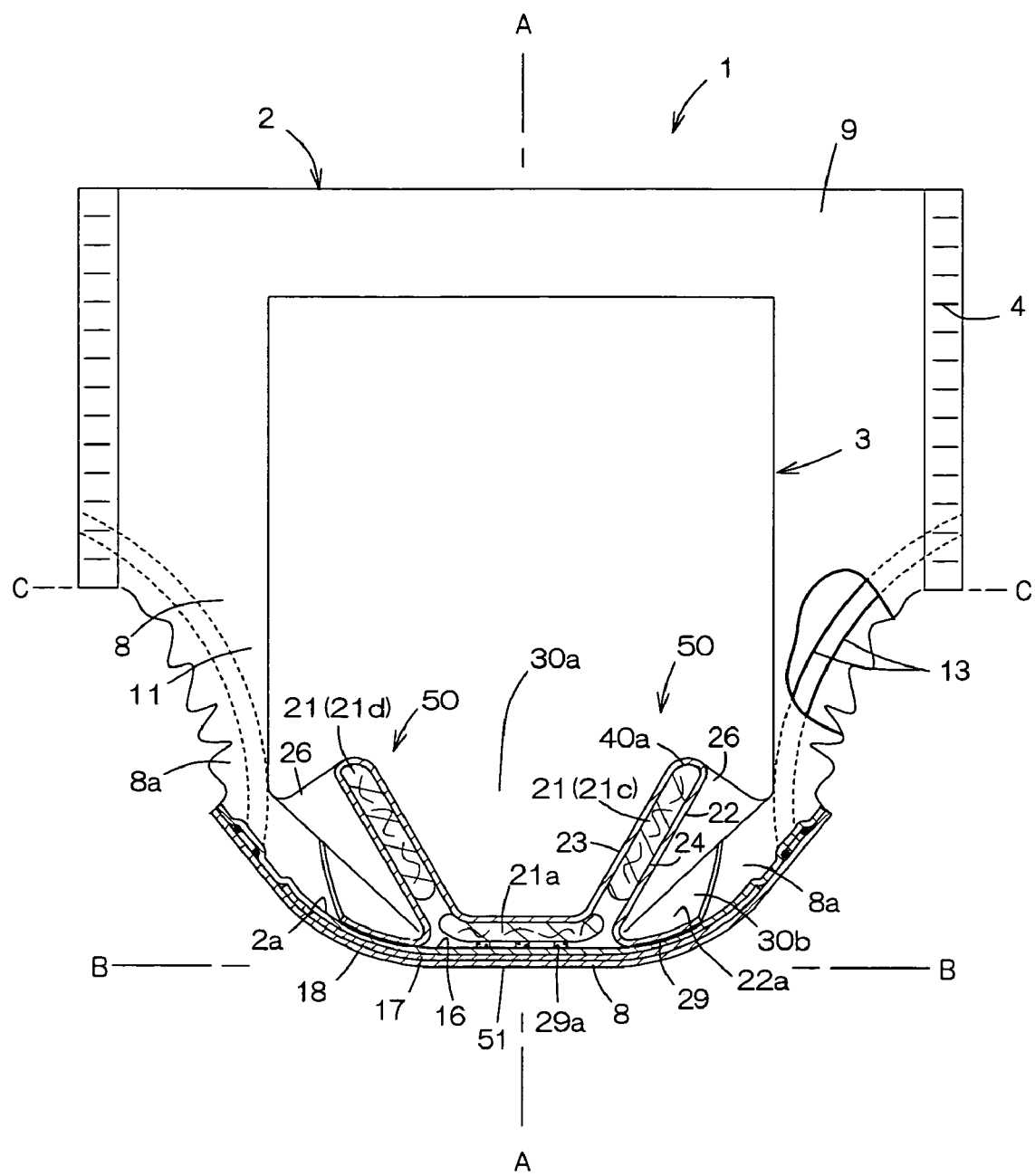
FIG. 3 is a sectional view taken along the line III-III in FIG. 1.

FIG. 1 is a perspective view of a pants-type disposable diaper 1, FIG. 2 is a partially cutaway perspective view of the diaper 1 of FIG. 1 and FIG. 3 is a sectional view taken along the line III-III in FIG. 1. A cross-section defined by the line III-III corresponds to a plane along which the diaper 1 of FIG. 1 is divided into a front waist region 6 and a rear waist region 7 and in which an internal structure of a bottom 51 of the diaper 1 appears. The diaper 1 has a height direction, a width direction and a back-and-forth direction which are orthogonal one to another. The height direction corresponds to a vertical direction in FIG. 1, the width direction corresponds to a direction extending along the line III-III in FIG. 1, in other words, a transverse direction in FIG. 3 and the back-and-forth direction corresponds to a direction indicated by arrows P and Q. The diaper 1 comprises a pants-type covering chassis 2 and a body fluid absorbent assembly 3 being capable of absorbing and containing bodily fluids discharged by a wearer. The covering chassis 2 has an inner surface 2a facing the skin of diaper wearer and an outer surface 2b facing a garment of wearer clothes and defines the front and rear waist regions 6, 7 adapted to cover the front and rear waist regions of the wearer, respectively, and a crotch region 8 adapted to cover the crotch region of the wearer. The front and rear waist regions 6, 7 are overlapped and bonded together in vicinities of transversely opposite side edges of the diaper 1 at a plurality of spots 4 arranged intermittently in the vertical direction of the diaper 1 so that these waist regions 6, 7 may define a waist-hole 9 and these waist regions 6, 7 may cooperated with the crotch region 8 to define a pair of leg-holes 11. The waist-hole 9 and the leg-holes 11 are provided in vicinities of peripheral edges thereof with a plurality of elastic members 12, 13, respectively, secured in a stretched state thereto. The body fluid absorbent assembly 3 lies on an inner surface 2a of the covering chassis 2 and extends over the crotch region 8 and further into the front and rear waist regions 6, 7. The body fluid absorbent assembly 3 curves in a generally U-shape with an inner surface thereof being mutually opposed to itself. The absorbent assembly 3 includes, in a vicinity of the bottom 51 of the diaper 1, a pair of folded portions 50 which are defined by transversely opposite side edges 26 partially folded inward as viewed in the width direction of the diaper 1 toward a longitudinal center line A-A (See FIG. 4 also) extending in the height direction so as to bisect the width of the diaper 1.

Figure 4:
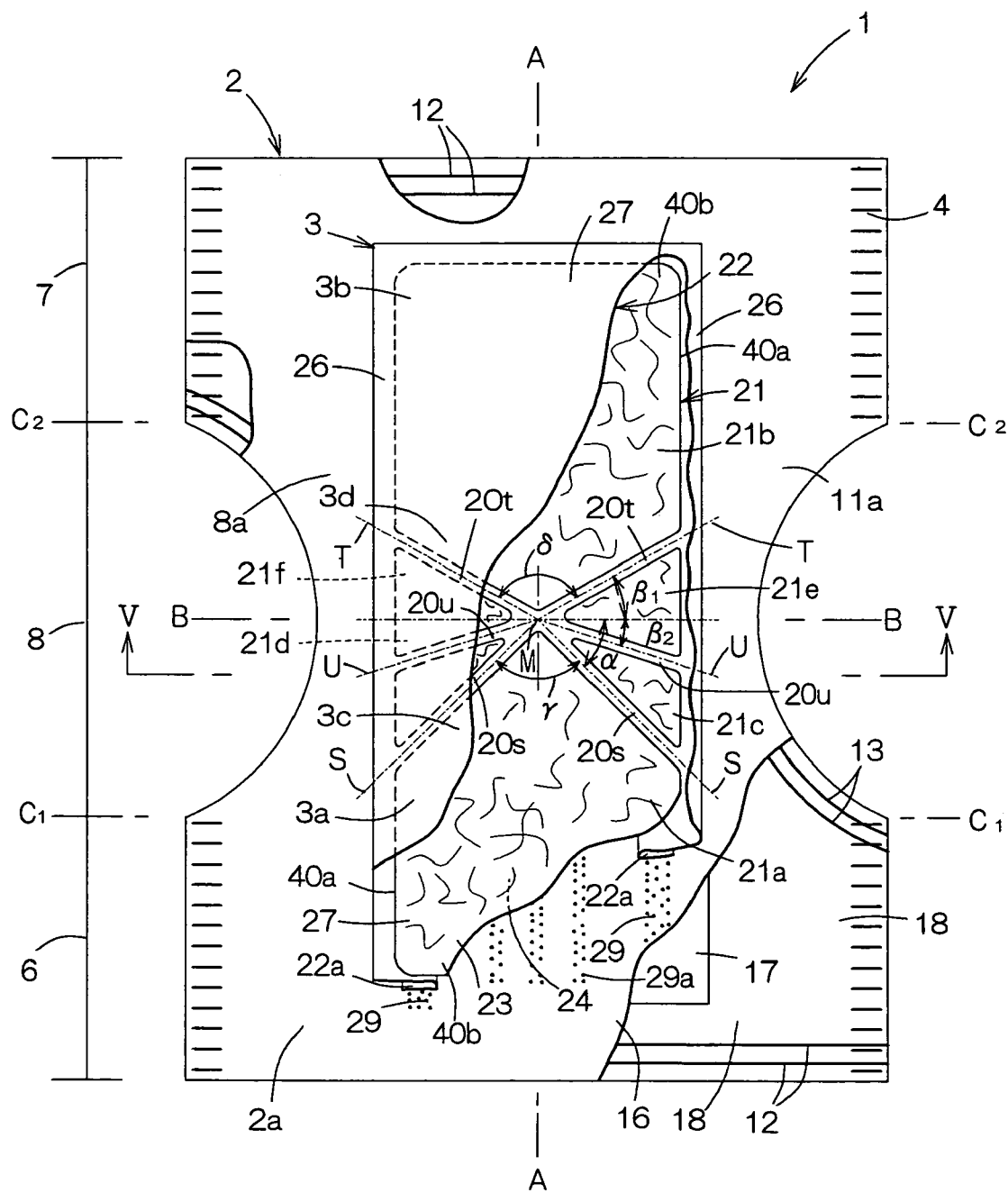
FIG. 4 is a developed plan view of the diaper of FIG. 1.
Figure 5:
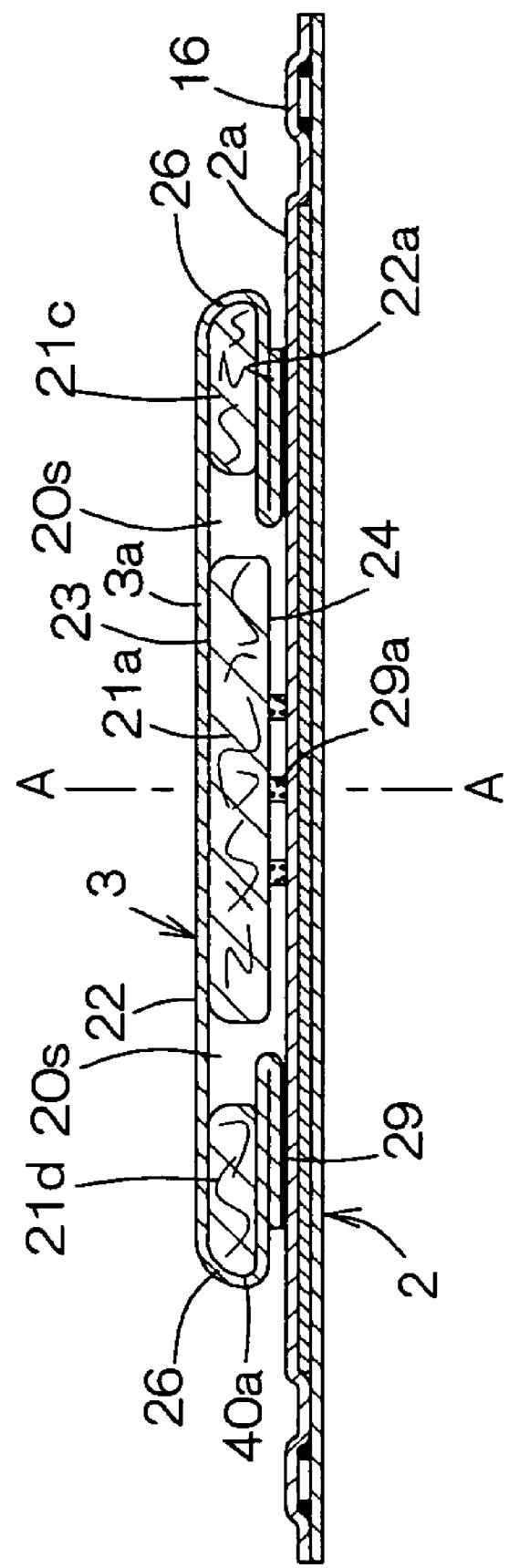
FIG. 5 is a sectional view taken along the line V-V in FIG. 4.

FIG. 4 is a plan view of the diaper 1 of FIG. 1 with the front and rear waist regions 6, 7 having been peeled off from each other at the bonded spots 4 and developed in the opposite directions indicated by the arrows P and Q as partially broken away and FIG. 5 is a sectional view taken along the line V-V in this plan view. In the diaper 1 developed in this manner, a crossline B-B is illustrated to extends across the diaper 1 and bisects a longitudinal dimension of the diaper 1. The crossline B-B intersects with the longitudinal center line A-A at its midpoint M. The diaper 1 of FIG. 4 is generally symmetric about the longitudinal center line A-A and folded inward along the crossline B-B to form the diaper 1 of FIG. 1, wherein the crossline B-B extends along the bottom 51 of the diaper 1 (See FIG. 3). The midpoint M of the longitudinal center line A-A coincides with a midpoint of the crossline B-B. Upper and lower lines $C_1$-$C_1$, and $C_2$-$C_2$ defining an extent of the crotch region 8 in FIG. 4 are superposed on each other to in the diaper 1 of FIG. 3 and define a single line C-C passing through crests of the respective leg-holes 11 in parallel to the crossline B-B.

The covering chassis 2 comprises, as illustrated by FIGS. 4 and 5, an hourglass-shaped inner sheet 16 made of a breathable nonwoven fabric, more preferably made of a hydrophobic breathable nonwoven fabric, an intermediate sheet 17 made of a liquid-impervious plastic film, more preferably made of a breathable liquid-impervious plastic film presenting a rectangular shape of a generally same size as a planar size of the absorbent assembly 3 or of a size larger than the planar size of the absorbent assembly 3 and lying on an outer surface of the inner sheet 16 and an outer sheet 18 made of a breathable nonwoven fabric and identical to the inner sheet 16 and lying on an outer surface of the intermediate sheet 17. These sheets 16, 17, 18 are laminated and intermittently bonded one to another by means of adhesives or suitable welding techniques. The inner sheet 16 and the outer sheet 18 constituting the covering chassis 2 contribute to a soft touch of this covering chassis 2. Waist and leg elastic members 12, 13 interposed between these inner and outer sheets 16, 18 are bonded to at least one of these sheets 16, 18 by means of adhesives (not shown).

The absorbent assembly 3 comprises a core 21 and a cover sheet 22 and presents a rectangular shape which is vertically longer in FIG. 4. The absorbent assembly 3 has a pair of transversely opposite side edges 26 extending generally parallel to the longitudinal center line A-A in the crotch region 8 and further into the front and rear waist regions 6, 7 and a pair of longitudinally opposite ends 27 extending generally in parallel to the crossline B-B across the diaper 1 (See FIG. 2 also). Term "generally" used herein suggests that these side edges 26 and ends 27 may rectilinearly extend or may slightly curve. For example, the side edges 26 may describe in the crotch region 8 curves which are convex toward the center line A-A. A crotch section of the absorbent assembly 3 is the section thereof lying in the crotch region 8 of the covering chassis 2. Referring to FIG. 4, this section is defined between a pair of parallel lines $C_1$-$C_1$ and $C_2$-$C_2$ and, referring to FIG. 3, this section is defined between the crossline B-B and the line C-C. The core 21 also has a generally rectangular shape as a whole and has an inner surface 23 facing skin of the wearer, an outer surface 24 facing a garment of the diaper wearer, transversely opposite lateral surfaces 40a connecting the inner and outer surfaces 23, 24 and extending in the longitudinal direction, and longitudinally opposite ends 40*b* transversely extending in the front and rear waist regions 6, 7, respectively. The core 21 further includes grooves 20*s*, 20*t* and 20*u* respectively extending along a pair of chain lines S which extend from the midpoint M on the longitudinal center line A-A to points on the side edges 26 lying aside toward the front waist region 6 in a generally V-shape, a pair of chain lines T which extend from the midpoint M to points on the side edges 26 lying aside toward the rear waist region 7 in a generally V-shape and a pair of chain lines U which extend between those chain lines S and T from the midpoint M to points on the side edges 26 lying aside toward the front waist region 6 (See FIG. 5 also). These grooves 20*s*, 20*t* and 20*u* divide the core 21 into core elements 21*a*, 21*b*, 21*c*, 21*d*, 21*e* and 21*f*. The crossline B-B crosses the chain lines S at an angle $\alpha$, the crossline B-B crosses the chain lines T at an angle $\beta_1$ and the crossline B-B crosses the chain lines U at an angle $\beta_2$. A preferred angle $\alpha$ is in a range of 35 to 60° and a preferred angle $\beta_1$ is in a range of 10 to 30°. As will be described in more detail with reference to FIG. 4, the angle $\beta_2$ is an angle automatically determined as the sections of the side edges 26 extending between the grooves 20*s* and the grooves 20*t* are folded along these grooves 20*s*, 20*t* inward with respect to the absorbent assembly 3 as best seen in FIGS. 2 and 3. In the crotch region 8 of the diaper. 1, the absorbent assembly 3 has its width narrower than that of the covering chassis 2 and the lateral zones 8*a* of the covering chassis 3 extending outside the side edges 26 of the absorbent assembly 3 form a pair of leg-surrounding flaps 11*a* adapted to fully encircle the respective leg-holes 11.

Each of the core elements 21*a*-21*f* is formed from compressing water absorbent material such as fluff pulp and/or super-absorbent polymer particles under an appropriate pressure and, if desired, wrapping the core element compressed in this manner with a tissue paper or a nonwoven fabric of thermoplastic synthetic fibers modified to be hydrophilic. The inner surface 23 of the core element 21*a*-21*f* or a tissue paper or the like (not shown) covering the inner surface 23 may be bonded to the cover sheet 22. The outer surface 24 of the core element 21*a*-21*f* or a tissue paper or the like covering the outer surface 24 may be bonded to the inner sheet 16 or the like by means of adhesives 29*a* (See FIG. 5). The cover sheet 22 transversely extends to cover the inner surface 23, the opposite lateral surfaces 40*a* and zones of the outer surface 24 contiguous to these lateral surfaces 40*a*. Below the outer surface 24, the transversely opposite side edges 22*a* of the cover sheet 22 are folded back outward in the transverse direction of the core 21 and bonded to the inner surface of the inner sheet 16 by means of hot melt adhesives 29. Portions of the cover sheet 22 extending outward beyond the longitudinally opposite ends 40*b* of the core 21 are bonded to the inner sheet 16 by means of hot melt adhesives (not shown). Thus, the cover sheet 22 is folded in a Z-shape or an inverted Z-shape in a vicinity of the lateral surfaces 40*a* of the core 21 (See FIGS. 4 and 5). Stock material for the cover sheet 22 may be selected from a liquid-pervious nonwoven fabric, a porous plastic film and a laminated sheet comprising these nonwoven fabric and film.

The diaper 1 having the absorbent assembly 3 formed as has been described above may be converted from the developed state as shown by FIG. 4 to the state as shown by FIG. 1 by folding the developed diaper 1 along the crossline B-B with the absorbent assembly 3 inside and bonding the front and rear waist regions 6, 7 together at the spots 4. In this course, portions of the absorbent assembly 3 lying in the crotch region 8 and divided by the longitudinal center line A-A in two are folded toward the longitudinal center line A-A, i.e., inwardly of the absorbent assembly 3. More specifically, the absorbent assembly 3 is folded inward along a pair of the grooves 20*s* serving as first folding guide lines as well as along a pair of the grooves 20*t* serving as second folding guide lines. Thereupon, the core elements 21*c*, 21*e* have their outer surfaces 24 (See FIG. 5) opposed to each other while the core elements 21*d*, 21*f* have their outer surfaces 24 opposed to each other and, at the same time, the inner surface 23 of the core element 21*a* is opposed to the inner surfaces 23 of the core elements 21*c*, 21*d* while the inner surface 23 of the core element 21*b* is opposed to the inner surfaces 23 of the core elements 21*e*, 21*f* (See FIG. 4). In this way, the absorbent assembly 3 is formed with a pair of the folded portions 50. The rectangular absorbent assembly 3 having been curved in a U-shape and folded inward along the grooves 20*s*, 20*t* may be further flatly folded until the inner surface of the absorbent assembly 3 substantially comes in contact with itself to settle folding guide lines along the grooves 20*u* which are positioned so that the core elements 21*c*, 21*e* having already been folded may be placed upon each other. The core 21 is absent or substantially absent in the grooves 20*s*, 20*t*, 20*u* of the absorbent assembly 3 destined to be folded in this manner. Therefore, these grooves 20*s*, 20*t*, 20*u* are less stiff than the remaining region and facilitate the absorbent assembly 3 to be folded therealong as illustrated by FIG. 2.

The absorbent assembly 3 is formed, as a result of folding, with a front waist side absorbent zone 3*a* in front of the folded portions 50 and a rear waist side absorbent zone 3*b* behind the folded portions 50 (See FIGS. 2 and 4). These front and rear waist side absorbent zones 3*a*, 3*b* are defined by non-folded portions, respectively. In the absorbent assembly 3, a crotch zone of the front waist side absorbent zone 3*a*, i.e., a zone 3*c* defined between a pair of the grooves 20*s* and the line $C_1$-$C_1$ in FIG. 4 should neither obstruct forward movement of the legs of the wearer when the wearer walks nor obstruct the movement of the leg's of the wearer when the wearer sits down with the legs stretched forward. To meet this requirement, the crossing angle $\alpha$ is set to be relatively large and an opening angle $\gamma$ between a pair of the chain lines S, S is set to be relatively small. The opening angle $\gamma$ is preferably in a range of 60 to 110°. Furthermore, in the absorbent assembly 3, a crotch zone of the rear waist side absorbent zone 3*b*, i.e., a zone 3*d* defined between a pair of the grooves 20*t* and the line $C_2$-$C_2$ should cover the his of the wearer as widely as possible. To meet such requirement, the crossing angle $\beta_1$ is set to be relatively small and an opening angle $\delta$ between a pair of the chain lines T, T is set to be relatively large. The opening angle $\delta$ is preferably in a range of 120 to 160°. In this way, it is unlikely that the front waist side absorbent zone 3*a* might obstruct the movement of the legs of the wearer and the rear waist side absorbent zone 3*b* might cause leakage of body fluids in a vicinity of the hip of the wearer.

As will be apparent from FIGS. 2 and 3, the absorbent assembly 3 is formed between the folded portions 50 with an inner side pocket 30*a* and between the respective lateral zones 8*a* of the covering chassis 2 and the absorbent assembly 3 with outer pockets 30*b*.

To put the diaper 1 according to the present invention on a child body, his or her mother may put the hands inside the peripheral edge of the waist-hole 9 and guide the legs of the child through the leg-holes 11 as the waist-hole 9 is being broadened. With the diaper 1 according to this embodiment, the deformation of the diaper 1 due to broadening of the waist-hole 9 is not transmitted to the portion of the absorbent assembly 3 lying in the crotch region 8 since the assembly 3 is provided independently from the covering chassis 2 and the crotch region 8 is remote from the waist-hole 9. Furthermore, the side edges 26 of the absorbent assembly 3 are not bonded to the lateral zones 8a, so the absorbent assembly 3 is substantially not moved even the lateral zones 8a of the crotch region 8 are moved as the leg-holes 11 are broadened. Consequently, it is unlikely that the folded portions 50 might get out of their shapes. It is possible without departing from the scope of the invention to form the absorbent assembly 3 by filling regions of the core 21 which extend along the chain lines S, T, U, respectively, with water-absorbent material, then locally applying the water-absorbent material in these regions with pressure or heating under pressure using suitable means such as embossing rolls so that these regions may have stiffness higher than that in the remaining region and the absorbent assembly 3 may be folded along these regions. It is also possible to fill the regions of the absorbent assembly 3 extending along the chain lines U with the absorbent material while the regions of the absorbent assembly 3 extending along the chain lines S, T may be left empty so as to form the grooves 20s, 20t and thereafter to form the folded portions 50. While the folding guide lines formed along the chain lines S, T preferably have sharp edges, it is not essential for the folding guide lines extending along the chain lines U to have sharp edges.

Figure 6:
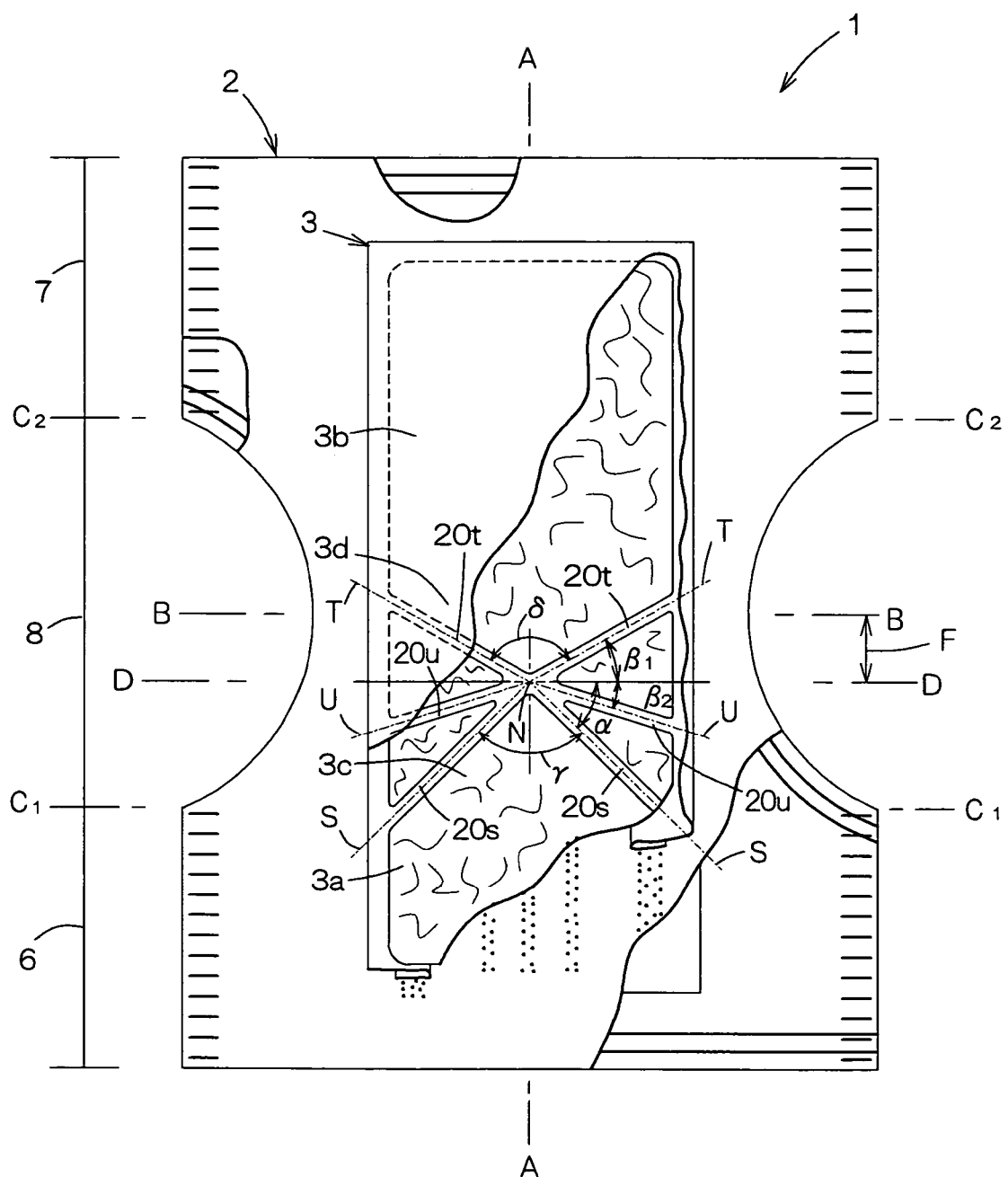
FIG. 6 is a view similar to FIG. 4 of one preferred embodiment of the invention.

FIG. 6 is a view similar to FIG. 4 of one preferred embodiment of the invention. In the case of the diaper 1 according to this embodiment, respective pairs of the grooves 20s, 20t, 20u are formed on the basis of a second crossline D-D placed aside from the crossline B-B toward the front waist region 6 by a distance F which is preferably in a range of 10 to 50 mm. The crossline D-D rectilinearly extends from a starting point N on the longitudinal center line A-A toward the transversely opposite side edges 26. From this starting point N, a pair of the chain lines S extend to the side edges 26 of the front waist region 6, a pair of the chain lines T extend to the side edges 26 of the rear waist region 7 and a pair of the chain lines U extend between the chain lines S and the chain lines T, respectively, to the side edges 26 of the front waist region 6. The respective chain lines S, T, U intersect the crossline D-D at angles $\alpha, \beta_1, \beta_2$, respectively. In this diaper 1, the folded portions 50 are formed more aside than in the embodiment shown by FIG. 4 toward the front waist region 6 and therefore it is possible to set the crossing angle $\alpha$ of the crossline D-D and the chain lines S to be equal to or larger than the crossing angle $\beta_1$ of the crossline D-D and the chain lines T. Even when the crossing angle $\alpha$ is equal to the crossing angle $\beta_1$, the absorbent assembly 3 has its width reduced in front of the crossline B-B bisecting the diaper 1 into front and rear halves and, in a consequence, an anxiety of obstructing forward movement of the legs of the wearer can be effectively alleviated. Such feature of this embodiment allows the crossing angle $\alpha$ to be equal to the crossing angle $\beta$ in a range of 10 to 30°. In this embodiment also, the crossing angle $\alpha$ may be set to a range of 35 to 60° and thereby the opening angle $\gamma$ may be correspondingly narrowed while the crossing angle $\beta$ may be set to a range of 35 to 60° and thereby the opening angle $\delta$ may be enlarged. In this way, the anxiety that the diaper 1 might obstruct the movement of the legs of the wearer can be further alleviated. With this diaper 1 also, the crotch zone 3c of the front non-folded portion defined between the line $C_1$-$C_1$ and a pair of the chain lines S of the absorbent assembly 3 has a relatively small extent and the crotch zone 3d of the rear non-folded portion defined between the line $C_2$-$C_2$ and a pair of the chain lines T has a relatively large extent.

Figure 7:
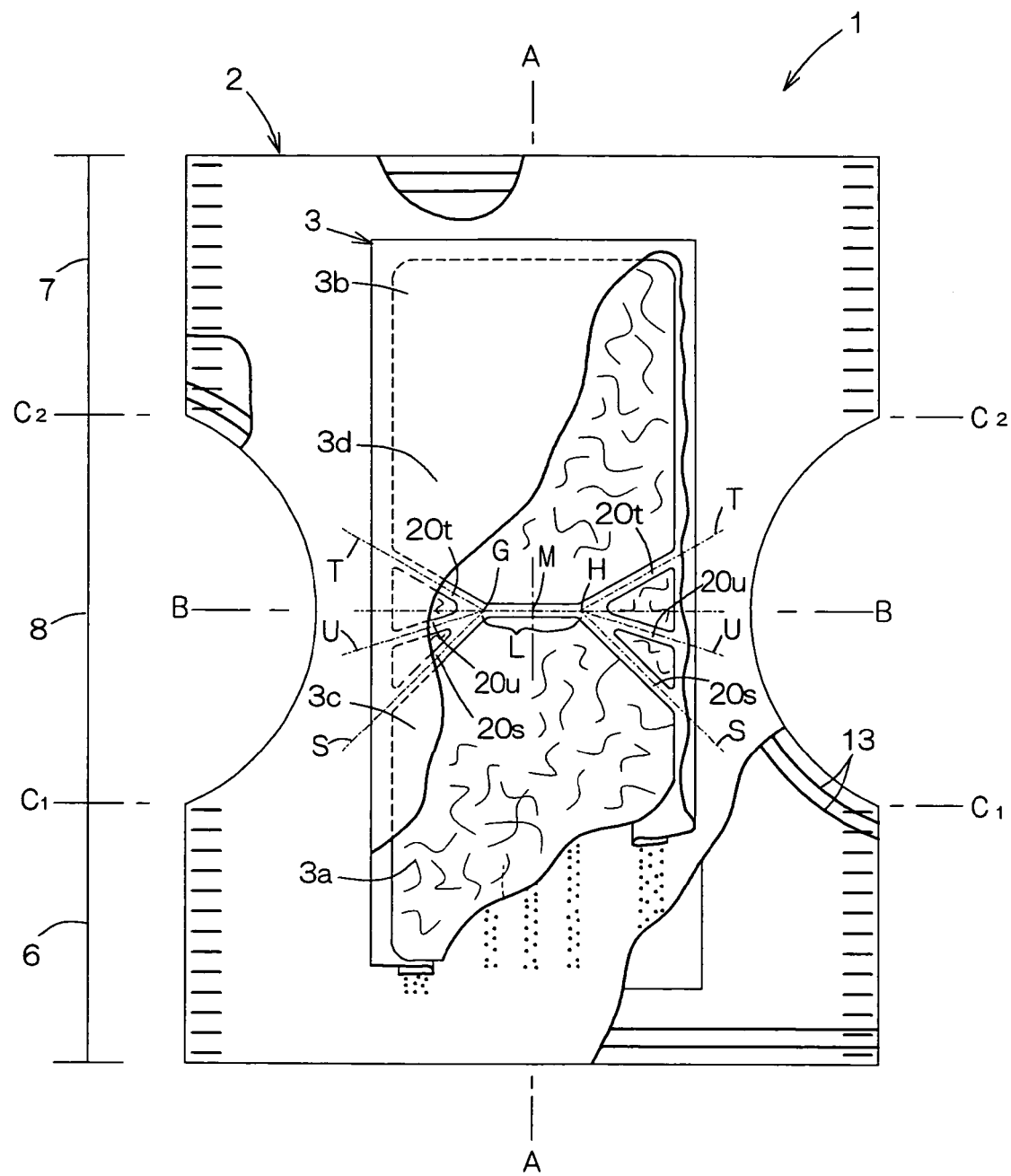
FIG. 7 is a view similar to FIG. 4 of another preferred embodiment of the invention.

FIG. 7 is a view similar to FIG. 4 of another preferred embodiment of the invention. In the absorbent assembly 3 of this diaper 1, the chain lines S, T, U and the grooves 20s, 20t, 20u extend from the transversely opposite side edges 26 from two starting points G, H on the crossline B-B which two starting points G, H are equidistant from the midpoint M of this crossing line B-B. Similarly in the case of the diaper 1 shown by FIG. 4, the absorbent assembly 3 is folded along the grooves 20s, 20t, 20u to form the folded portions 50. A section L extending between two points G and H on the crossing line B-B defines a boundary line of the front waist side absorbent zone 3a and the rear waist side absorbent zone 3b. The section L may have an appropriate dimension of 0 mm or larger depending on a size of the diaper 1 to form effective folded portions 50 selected. When the section L has the dimension of 0 mm, those two points G and H coincide with the midpoint M, resulting in the diaper 1 shown by FIG. 4.

The present invention may be exploited in manners different from the embodiments which have been described above in reference with FIGS. 1 through 7. For example, the invention may be exploited in a manner such that the crotch region 8 of the covering chassis 2 has a width equal to or smaller than the width of the absorbent assembly 3 in the state illustrated by FIG. 4. In this alternative embodiment, the absorbent assembly 3 may be formed from the core 21 having the outer surface 24 covered with a liquid-impervious sheet which is, in turn, bonded to the covering chassis 2 so that the absorbing assembly 3 may be bonded to the covering chassis 2 in the front and rear waist regions 6, 7 but not in the crotch region 8. Such embodiment of the diaper 1 may be further modified by cutting the crotch region 8 away from the covering chassis 2. While the invention has been described above with respect to the diaper 1 as one embodiment, the invention is applicable also to the other wearing articles such as training pants, incontinence pants and sanitary pants.

The disposable pants-type wearing article according to the present invention is primarily characterized in that, even when the body fluid absorbent assembly formed with the folded portions in the crotch region, the non-folded portion extending in front of the folded portions in the crotch region has a relatively small extent and the non-folded portion extending behind the folded portions has a relatively large extent. Therefore, it is unlikely that the front waist side absorbent zone of the body fluid absorbent assembly might obstruct free movement of the legs of the wearer and the rear waist side absorbent zone of the body fluid absorbent assembly might cause leakage of body fluids.

What is claimed is:
1. A disposable pants-type wearing article, comprising:
a front waist region, a rear waist region and a crotch region, said crotch region being provided with a body fluid absorbent assembly extending over said crotch region and further into said front and rear waist regions;
said body fluid absorbent assembly having transversely opposite side edges extending generally parallel to each other into said front and rear waist regions and longitudinally curving in a generally U-shape with an inner surface thereof opposed to itself in said front and rear waist regions;
wherein, in said crotch region, said body fluid absorbent assembly has:

a pair of first folding guide lines extending from either a midpoint of a crossline extending across said crotch region or from two points on said crossline, which are equidistant in opposite directions from said midpoint, to said transversely opposite side edges of said body fluid absorbent assembly, respectively, wherein said first folding guide lines diverge toward said front waist region and are inclined at a crossing angle α with respect to said crossline, a pair of second folding guide lines extending from said midpoint or said two points to said transversely opposite side edges of said body fluid absorbent assembly, respectively, wherein said second folding guide lines diverge toward said rear waist region and are inclined at a crossing angle β with respect to said crossline, a pair of folded portions defined between said first and second folding guide lines, wherein said body fluid absorbent assembly is folded inwardly along said first and second folding guide lines to define said folded portions, a first non-folded portion extending from said first folding guide lines toward said front waist region, and a second non-folded portion extending from said second folding guide lines toward said rear waist region; and wherein said body fluid absorbent assembly is configured so that said first non-folded portion has a relatively small extent and said second non-folded portion has a relatively large extent; and wherein each of said non-folded portions extends continuously without being folded from one of the transversely opposite side edges of said body fluid absorbent assembly to the other, and from the respective first or second folding guide lines to one of longitudinally opposite end edges of said body fluid absorbent assembly in the respective front or rear waist region.

2. The pants-type wearing article according to claim 1, wherein said crossline extends across a bottom of said crotch region as viewed in a vertical direction of said wearing article and said crossing angle α is larger than said crossing angle β.

3. The pants-type wearing article according to claim 1, wherein said crossline is closer to said front waist region than to said rear waist region, and said crossing angle α is equal to or larger than said crossing angle β.

4. The pants-type wearing article according to claim 2, wherein said crossing angle α is in a range of 35 to 60° and said crossing angle β is in a range of 10 to 30°.

5. The pants-type wearing article according to claim 3, wherein said crossline is spaced from a center line bisecting a length of said article by 10 to 50 mm.

6. The pants-type wearing article according to claim 1, wherein
said first folding guide lines extend from said two points on said crossline toward said front waist region; and
said body fluid absorbent assembly is further folded along a section of said crossline between said two points.

7. The pants-type wearing article according to claim 1, wherein said body fluid absorbent assembly further comprises a pair of third folding guide lines extending from said midpoint or said two points to said transversely opposite side edges of said body fluid absorbent assembly, respectively;
each of said third folding guide lines being located between one of the first folding guide lines and one of the second folding guide lines; and
wherein said body fluid absorbent assembly is folded outwardly along said third folding guide lines.

8. The pants-type wearing article according to claim 7, wherein all said first, second and third folding guide lines are oblique to said crossline.

9. The pants-type wearing article according to claim 8, wherein said first and third folding guide lines extend from said midpoint or said two points towards said front waist region, whereas said second folding guide lines extend from said midpoint or said two points towards said rear waist region.

10. A disposable pants-type wearing article having a longitudinal direction and a transverse direction perpendicular to the longitudinal direction, said article comprising:
a front waist region, a rear waist region and a crotch region extending in the longitudinal direction between said front and rear waist regions; and
a body fluid absorbent assembly extending over said crotch region and into said front and rear waist regions, and having transversely opposite side edges and longitudinally opposite front and rear end edges;
wherein said body fluid absorbent assembly has:
in said crotch region, a middle zone between said side edges;
a pair of first folding guide lines extending from said middle zone, toward the front waist region, and to the side edges of the absorbent assembly, respectively; and
a pair of second folding guide lines extending from said middle zone, toward the rear waist region, and to the side edges of the absorbent assembly, respectively;
wherein said body fluid absorbent assembly is folded inwardly along said first and second folding guide lines;
wherein a first angle defined between the first folding guide lines is smaller than a second angle defined between the second folding guide lines;
wherein said body fluid absorbent assembly further comprises:
a pair of folded portions each being defined by one of the side edges of the absorbent assembly and the associated ones of said first and second folding guide lines; and
a rear non-folded portion defined by the side edges of the absorbent assembly, the second folding guide lines, and the rear end edge of the absorbent assembly; and
wherein an entirety of said rear non-folded portion extends continuously without being folded from one of the transversely opposite side edges of said body fluid absorbent assembly to the other, and from the second folding guide lines to the rear end edge of said body fluid absorbent assembly.

11. The pants-type wearing article according to claim 10, wherein said body fluid absorbent assembly further comprises:
a front non-folded portion defined by the side edges of the absorbent assembly, the first folding guide lines, and the front end edge of the absorbent assembly;
wherein an entirety of said front non-folded portion extends continuously without being folded from one of the transversely opposite side edges of said body fluid absorbent assembly to the other, and from the first folding guide lines to the front end edge of said body fluid absorbent assembly.

12. The pants-type wearing article according to claim 10, wherein said body fluid absorbent assembly further comprises:
a pair of third folding guide lines extending from said middle zone to said transversely opposite side edges of said body fluid absorbent assembly, respectively;

each of said third folding guide lines being located between one of the first folding guide lines and one of the second folding guide lines; and said body fluid absorbent assembly being further folded outwardly along said third folding guide lines.

13. The pants-type wearing article according to claim 12, wherein said third folding guide lines extend from said middle zone towards said front waist region.

14. The pants-type wearing article according to claim 10, wherein said body fluid absorbent assembly further comprises a transverse folding guide line extending in the transverse direction and having opposite ends inwardly spaced from the side edges of the absorbent assembly, respectively;

each of the first folding guide lines and the associated one of the second folding guide lines diverge towards the associated one of the side edges of the absorbent assembly from one of the opposite ends of said transverse folding guide line; and the absorbent assembly is further folded inwardly along said transverse folding guide line.

15. The pants-type wearing article according to claim 14, wherein said body fluid absorbent assembly further comprises:

a pair of third folding guide lines each extending from one of the opposite ends of said transverse folding guide line, towards the front waist region, and to the respective one of the side edges of said absorbent assembly;

each of said third folding guide lines being located between one of the first folding guide lines and one of the second folding guide lines; and said body fluid absorbent assembly being further folded outwardly along said third folding guide lines.

16. The pants-type wearing article according to claim 14, wherein said transverse folding guide line is closer to the front end edge of said absorbent assembly than to the rear end edge of said absorbent assembly.

* * * * *